(12) United States Patent
Vinten-Johansen

(10) Patent No.: US 7,972,311 B2
(45) Date of Patent: Jul. 5, 2011

(54) CARDIOPLEGIA CATHETER SYSTEM

(75) Inventor: Jakob Vinten-Johansen, Grayson, GA (US)

(73) Assignee: Emory University, Atlanta, GA (US)

( * ) Notice: Subject to any disclaimer, the term of this patent is extended or adjusted under 35 U.S.C. 154(b) by 900 days.

(21) Appl. No.: 11/579,304

(22) PCT Filed: May 5, 2005

(86) PCT No.: PCT/US2005/015655
§ 371 (c)(1),
(2), (4) Date: Oct. 18, 2007

(87) PCT Pub. No.: WO2005/110026
PCT Pub. Date: Nov. 24, 2005

(65) Prior Publication Data
US 2008/0097383 A1 Apr. 24, 2008

(51) Int. Cl.
*A61M 5/32* (2006.01)
(52) U.S. Cl. .................................................. 604/175
(58) Field of Classification Search ............ 604/167.06, 604/168.01, 174, 175, 177, 179; 606/139, 606/144–146, 148
See application file for complete search history.

(56) References Cited

U.S. PATENT DOCUMENTS

| | | | |
|---|---|---|---|
| 5,013,296 A | | 5/1991 | Buckberg et al. |
| 5,741,234 A | * | 4/1998 | Aboul-Hosn ................. 604/174 |
| 5,814,065 A | * | 9/1998 | Diaz ............................. 606/213 |
| 6,176,851 B1 | | 1/2001 | Tsugita et al. |
| 6,254,573 B1 | * | 7/2001 | Haim et al. .................... 604/157 |
| 6,350,252 B2 | * | 2/2002 | Ray et al. ....................... 604/107 |
| 6,533,759 B1 | * | 3/2003 | Watson et al. ........... 604/167.02 |
| 7,390,328 B2 | * | 6/2008 | Modesitt ....................... 606/144 |

OTHER PUBLICATIONS 05742355.0, EP, Mar. 10, 2020, 94(3) EPC Communication for coorresponding appln.
05742355.0, EP, Dec. 22, 2009, Supplemental Search Report.
Medtronic Cardiovascular Cannula Products, 2009, Medtronic DLP Aortic Root Cannulae and DLP Aortic Root Cannulae with Vent; pp. IV-2, IV-3.

* cited by examiner

*Primary Examiner* — Nicholas D Lucchesi
*Assistant Examiner* — Nathan R Price
(74) *Attorney, Agent, or Firm* — Randi Isaacs; Emory University Patent Group

(57) ABSTRACT

A cardioplegia catheter system for delivery of a cardioplegia solution, comprising a cardioplegia catheter comprising an elongate tubular catheter body that defines a continuous central lumen and a flange that is connected to and extends therefrom an exterior surface of the catheter body, the flange defining a plurality of suture openings that extend therethrough the flange from a top surface to a bottom surface thereof. The cardioplegia system further comprising at least one stay suture and at least one suture capture stylet having a distal portion that is adapted to extend through one suture opening of the plurality of suture openings in the flange of the catheter body, wherein the distal portion of the rod has a shape that is adapted for slideably grasping a portion of the at least one stay suture.

39 Claims, 10 Drawing Sheets

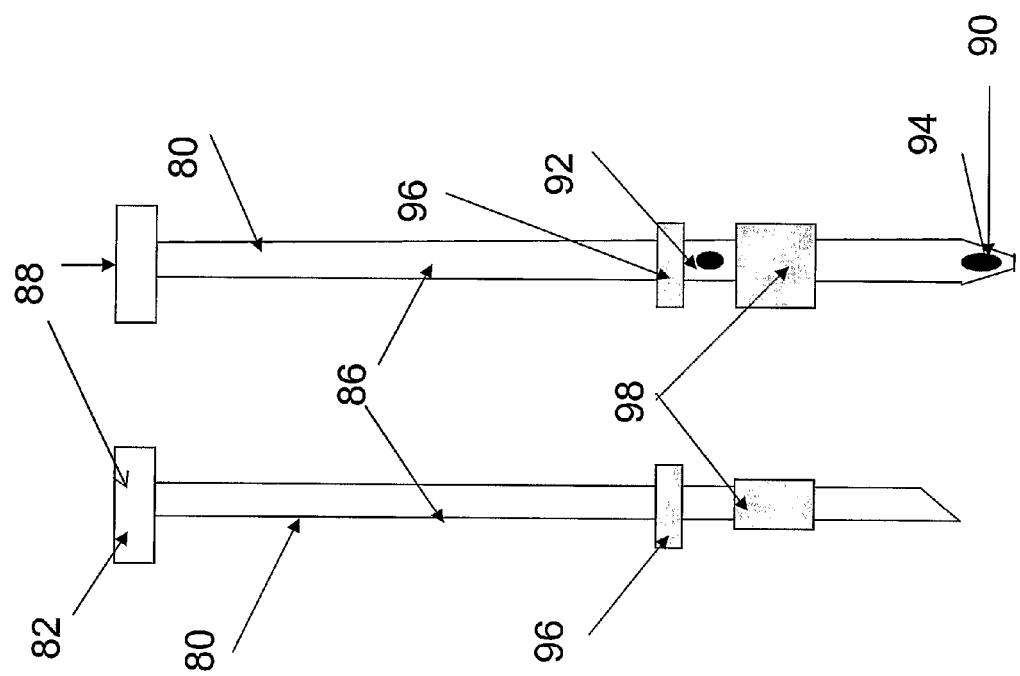

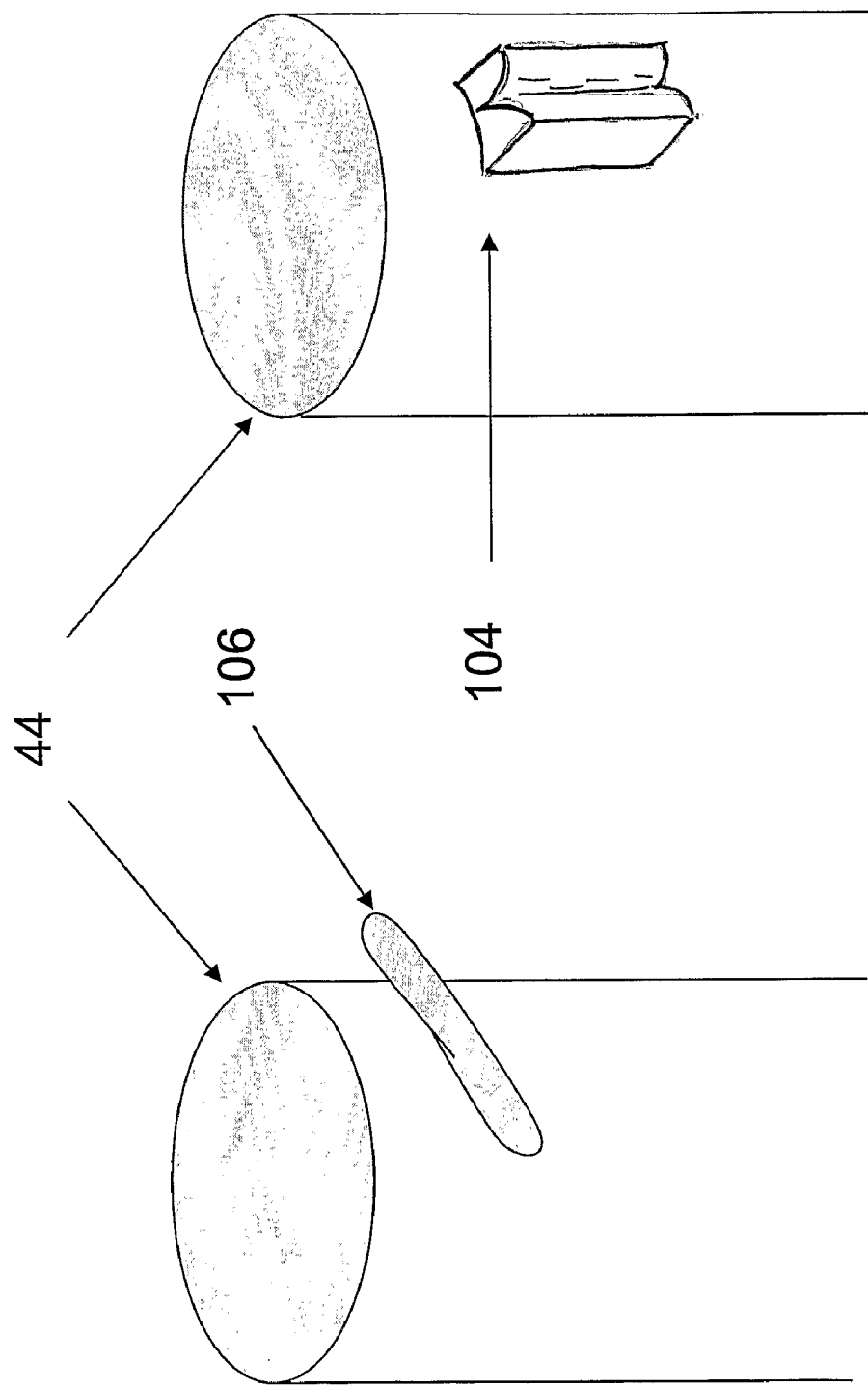

CARDIOPLEGIA CATHETER SYSTEM

FIELD OF THE INVENTION

The present invention relates generally to methods and devices for performing surgical procedures. More particularly, it relates to methods and systems for inducing chemical cardioplegic arrest and delivery of myocardial protection during cardiac surgery by antegrade perfusion of the coronary arteries from a peripheral arterial entry point.

BACKGROUND OF THE INVENTION

Myocardial protection is an essential part of almost every cardiac surgery procedure. Many cardiac surgery procedures cannot be effectively performed on a beating heart because the motion of the heart muscle would interfere with the intricate surgical manipulations. Also, for procedures where the coronary arteries or one of the chambers of the heart must be opened, the blood pressure in the beating heart would cause excessive bleeding that would endanger the patient and obscure the surgical site.

For most cardiac surgery procedures, it is preferable to stop the heart from beating for a period of time so that the surgery can be performed while on cardiopulmonary bypass. It is important that the heart muscle or myocardium be protected and supported during the time that the heart is stopped so that it does not suffer cellular damage that would prevent the heart from working properly when it is started again. There are numerous aspects to the process of myocardial protection including: (1) reducing the oxygen demand of the heart muscle; (2) adequately oxygenating the heart muscle and maintaining the proper chemical balance so that cellular damage does not occur, and 3) introducing drugs and mechanical maneuvers that protect the heart.

There are two approaches currently used to reduce the oxygen demand of the heart muscle. The first is to stop the heart from beating by cardioplegic arrest. The second is to reduce the temperature of the heart muscle to reduce the oxygen demand, i.e. hypothermia. Currently preferred procedures combine these two approaches in a method known as cold cardioplegia (cardio=heart; plegia=paralysis). However, some surgeons use a warmer cardioplegia solution to arrest and protect the heart, but this warmer solution must be given more frequently or continuously throughout the surgery.

Typically, when open heart surgery is performed, the chest is opened using a median sternotomy to gain surgical access to the heart. This also allows access to the aorta for cross clamping, which is important for standard methods of administering cardioplegia because it effectively separates the heart circulation from that of the rest of the body. Before stopping the heart, the patient is prepared by placing an arterial cannula and a venous cannula which are connected to a cardiopulmonary bypass (CPB) system. The CPB system takes over the functions of the heart and the lungs of the patient by oxygenating and pumping the blood while the heart is stopped. Once the CPB system is connected and started, the ascending aorta can be cross clamped to isolate the coronary arteries from the rest of the systemic arterial circulation. Then, cardioplegic arrest is induced by injecting a prescribed quantity of cardioplegic solution into the aortic root proximal to the heart using a needle or cannula which pierces the wall of the ascending aorta proximal to the cross clamp. To stop the heart (cardioplegia), a solution is infused through a catheter placed in the proximal aortic root to be distributed to the heart via the coronary arteries selectively. After the induction of cardioplegic arrest, the surgeon may infuse solution intermittently (for example, every 20-30 minutes) to refresh the previous solution residing in the heart muscle, or the solution may be infused continuously (or nearly so) via a catheter placed in the coronary sinus. Whichever option is used, many surgeons deliver a final dose of cardioplegia solution through the aortic root catheter as a "terminal" cardioplegia before the cross-clamp is removed from the aorta, and systemic blood flow is restored to the heart (reperfused). After the surgery is completed, the needle puncture in the aorta must be repaired before the heart is restarted.

The construction and use of catheters and related medical devices is well known. As noted above, current technologies allow for the delivery of cardioplegia solutions to patients undergoing cardiac surgery. The cardioplegia solution, for example, a high potassium concentration solution, may be administered to the patient's heart in an antegrade direction through the patient's aorta, i.e., in the direction of normal patient blood flow. Conventional antegrade cardioplegia techniques require the use of a catheter lumen, multiple rummels and associated hemostats for securing the rummel sutures and for maintaining hemostasis around the insert of the catheter lumen and the aortic wall interface. The sheer number of "devices" typically required to accomplish the administration of the cardioplegia solution clutters the operative field. Of course, it is contemplated that solutions of other composition, i.e. non-depolarizing cardioplegia solutions with arresting agents other than potassium, may be infused through the cardioplegia catheter described herein.

What is needed, therefore, is a cardioplegia catheter system constructed and arranged to permit the controlled antegrade delivery of a cardioplegia solution into the aortic root of a patient that does not interfere with the visibility of the surgical field. Such a catheter system organizes and reduces the clutter in the operative field.

SUMMARY

The present invention overcomes some of the design deficiencies of the known cardioplegia delivery systems by providing a cardioplegia catheter system adapted for the controlled delivery of fluids therethrough and into the aortic arch, specifically allowing delivery of a cardioplegia solution at known fluid pressures into the distal artery. The cardioplegia catheter system of this invention includes a cardoplegia catheter, at least one stay suture, and at least one suture capture stylet.

The catheter has an elongate tubular body that defines a continuous central lumen extending through the catheter body from a proximal end to a spaced distal end thereof. A fluid-tight connector, which may for example comprise a luer-type connector, is provided at the proximal end of the tubular body and is in fluid communication with the central lumen. A flange is connected and extends from the exterior surface of the catheter body intermediated a tapered portion of the distal end of the catheter body and the proximal end of the catheter body. The flange defines a plurality of suture openings extending between a top surface and a bottom surface of the flange. The catheter also includes a plurality of suture lumens that are connected to and are spaced about the exterior surface of the catheter body. The first end of each suture lumen is connected to the top surface of the flange in overlying registration with one suture opening in the flange. The catheter further includes a means for releasably securing and fixing a portion of a stay suture relative to the catheter.

Each suture capture stylet has a rod extending from a handle that is adapted to fit within one of the suture lumens of the catheter. A shaped portion of the distal end of the rod is sized so that it can be drawn through the suture opening in the flange and through the interior of the suture lumen. The shaped portion of the distal end of the rod is constructed and arranged for slideably grasping a portion of a stay suture.

BRIEF DESCRIPTION OF THE DRAWINGS

These and other features and aspects of the present invention will become better understood with reference to the following description, appended claims, and accompanying drawings, where:

FIG. 9 is a side view of the insert needle of the cardioplegia catheter system.

FIG. 10 is front view of the insert needle of FIG. 9.

FIG. 11 is a partial perspective view of a bar member for securing a portion of a stay suture to a portion of a suture lumen.

FIG. 12 is a partial perspective view of a clip for securing a portion of a stay suture to a portion of a suture lumen.

DETAILED DESCRIPTION OF THE INVENTION

Figure 1:
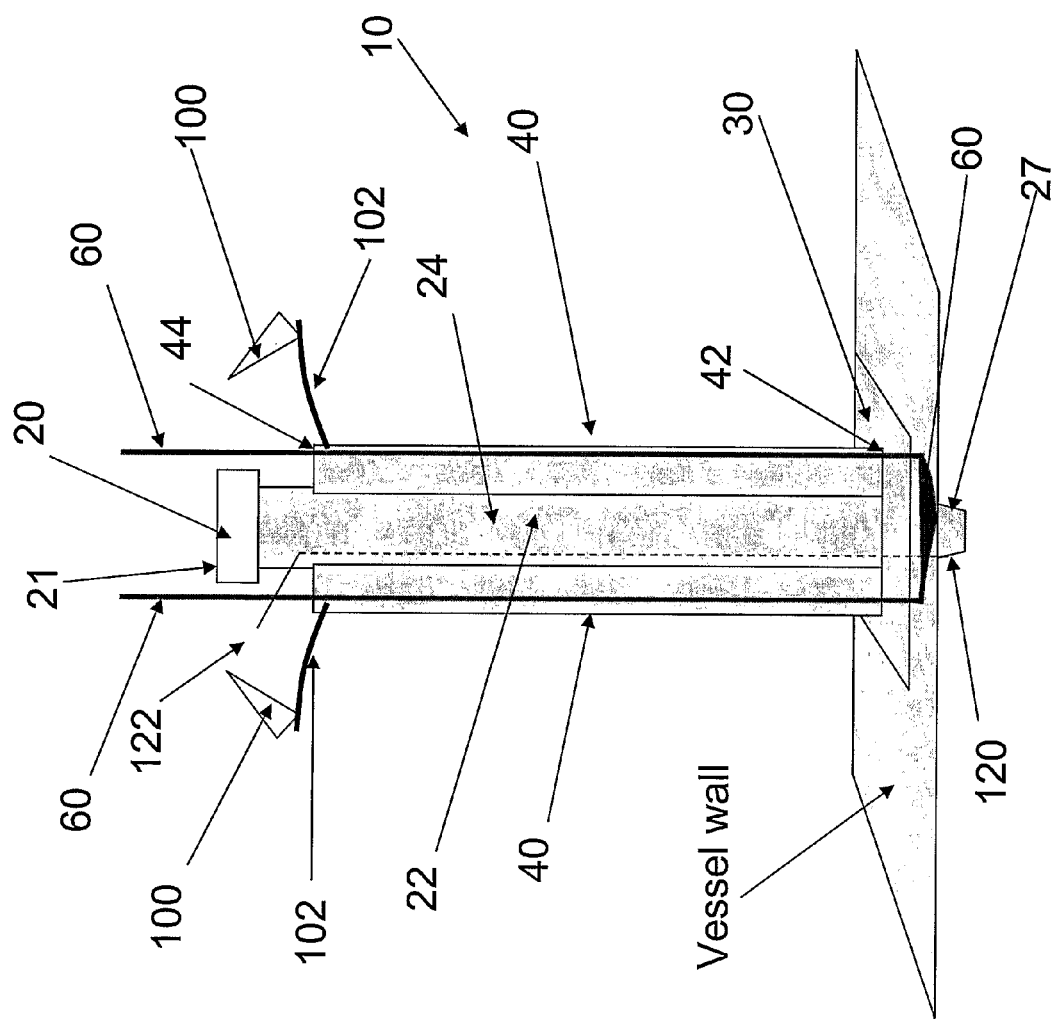
FIG. 1 is partially cutaway perspective view of a first embodiment of the cardioplegia catheter system of the invention, showing a cardioplegia catheter positioned onto a puncture wound in an aortic vessel and a pair of stay sutures extending through a pair of suture lumens formed thereon the catheter. It is contemplated that one or more stay sutures may be used to operatively connect the cardioplegia catheter and the aorta.
Figure 2:
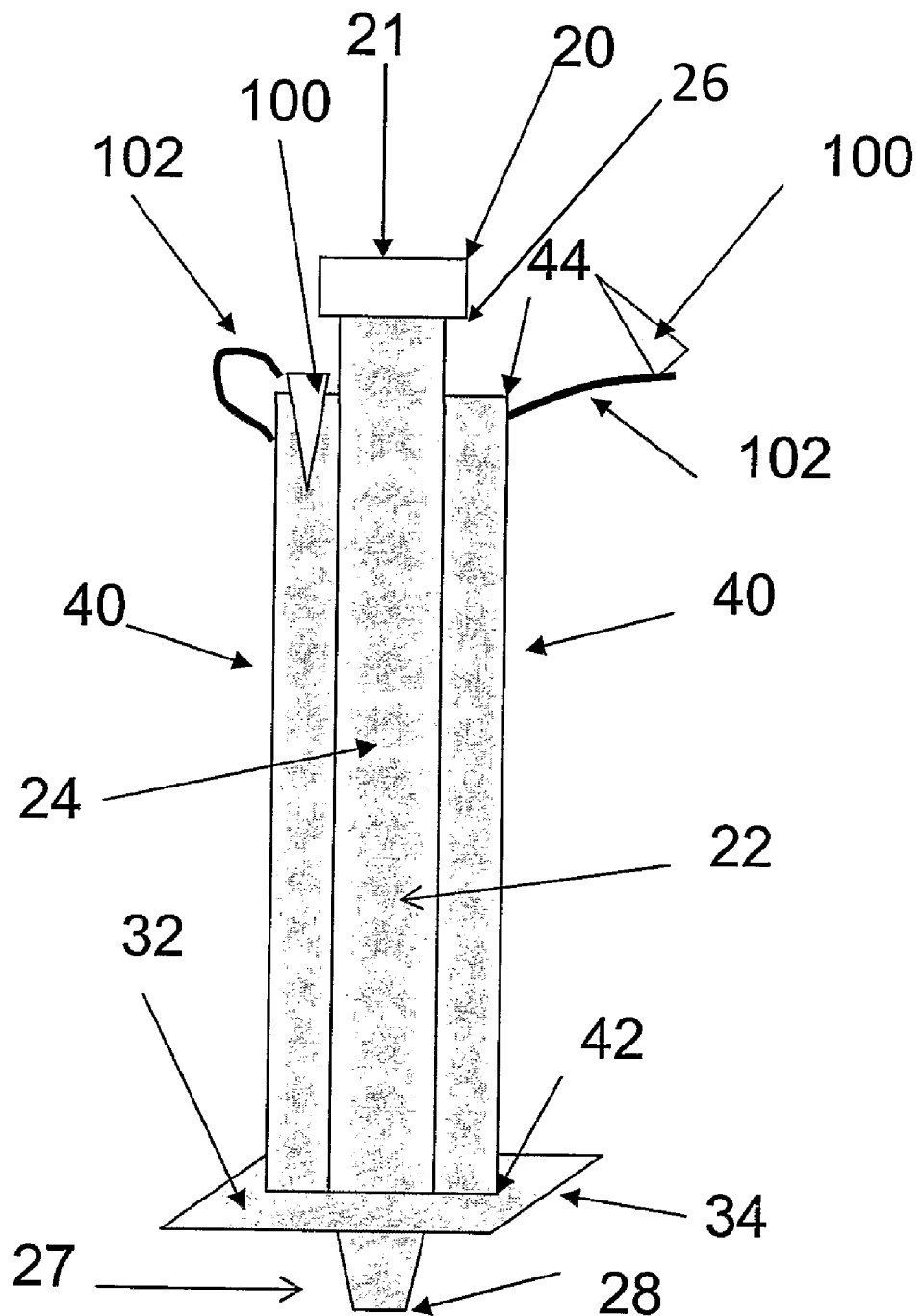
FIG. 2 is a perspective view of the cardioplegia catheter system of FIG. 1.
Figure 3:
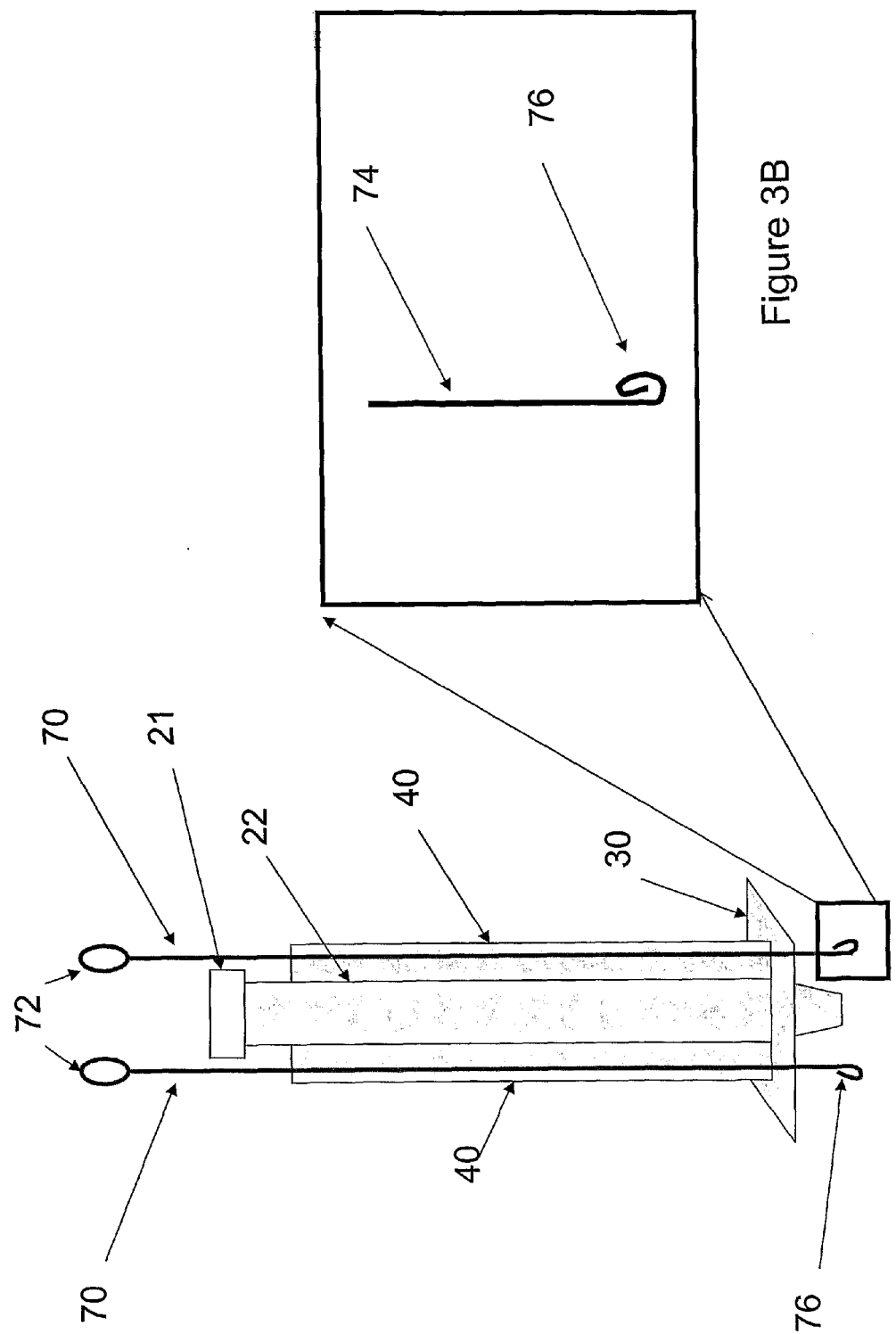
FIG. 3A is a partial cutaway perspective view of the cardioplegia catheter system of FIG. 1, showing an exemplary suture capture stylet extending through each of the pair of suture lumens.
FIG. 3B is a partial enlarged view of an exemplary distal portion of the suture capture stylet of FIG. 3A.
Figure 4:
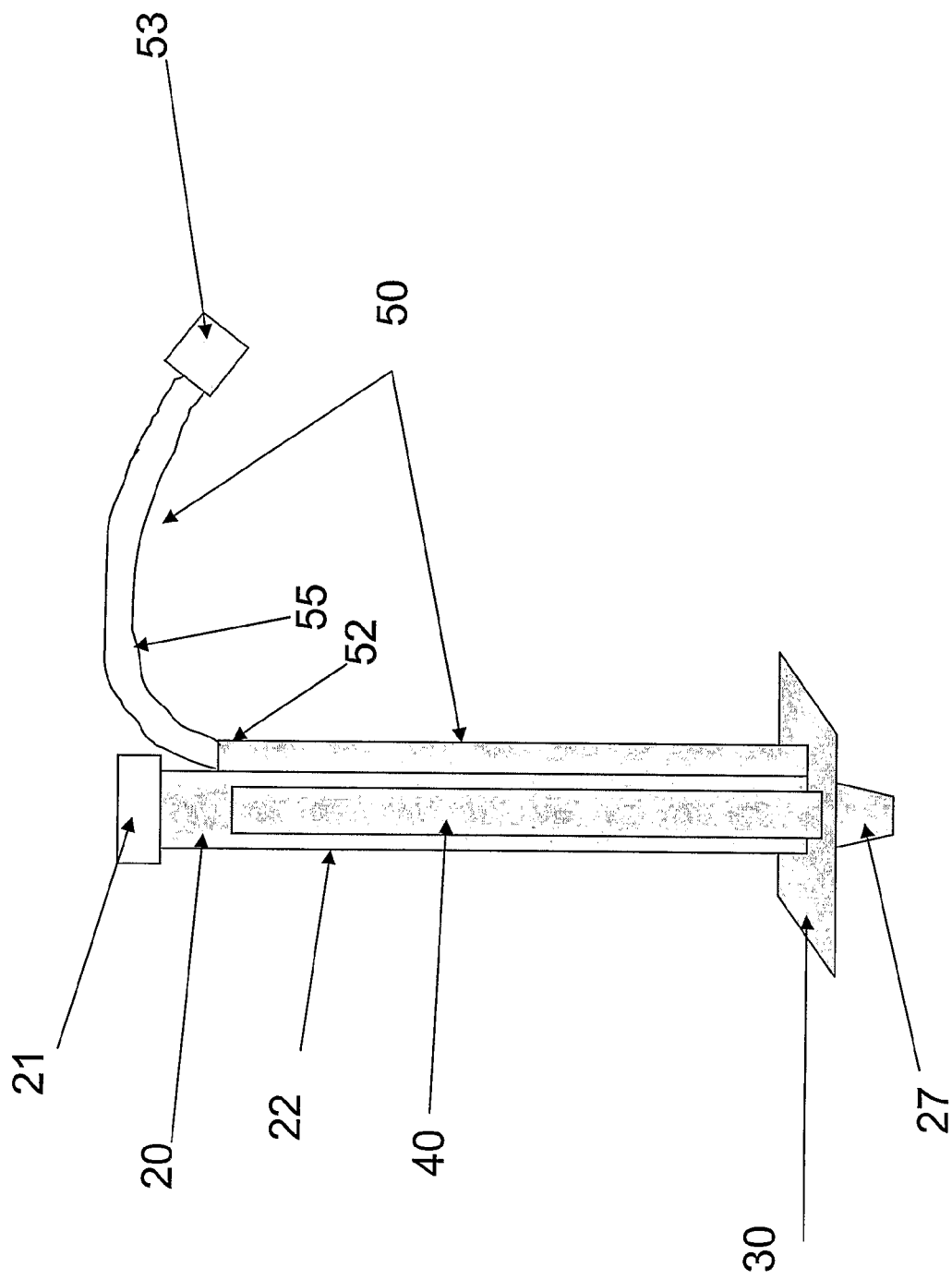
FIG. 4 is a side perspective view of the cardioplegia catheter system of FIG. 1, showing a pressure lumen formed therein.
Figure 5:
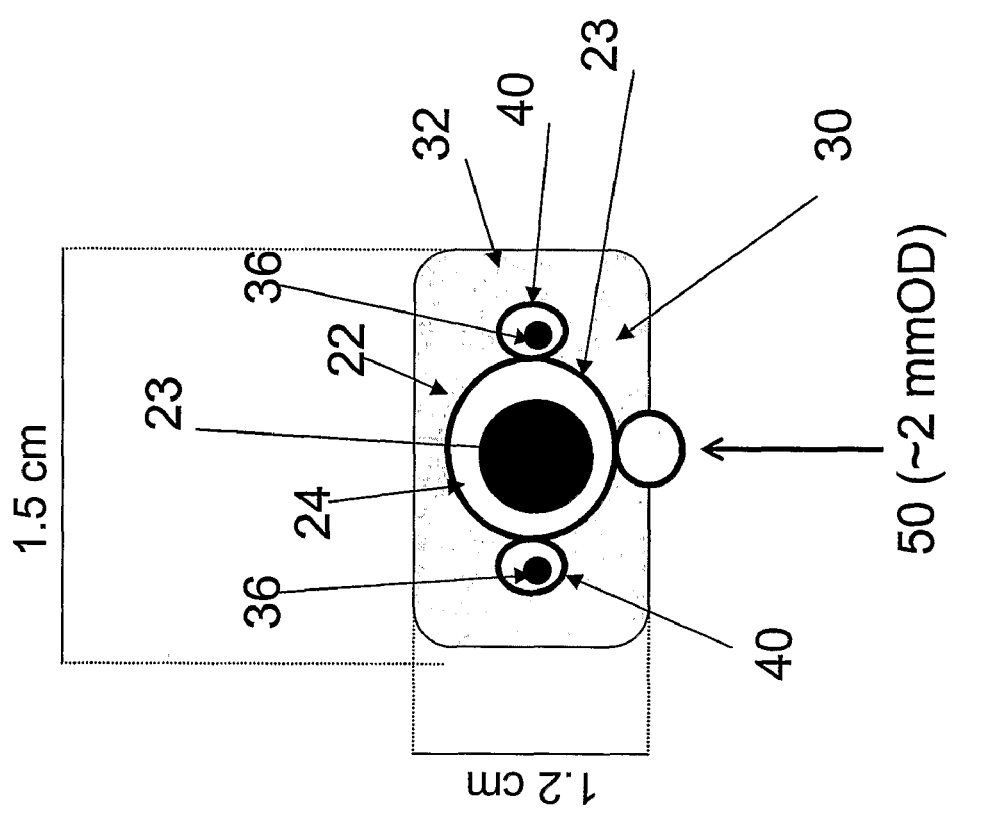
FIG. 5 is a plan top view of the proximal end of the cardioplegia catheter of FIG. 1.
Figure 6:
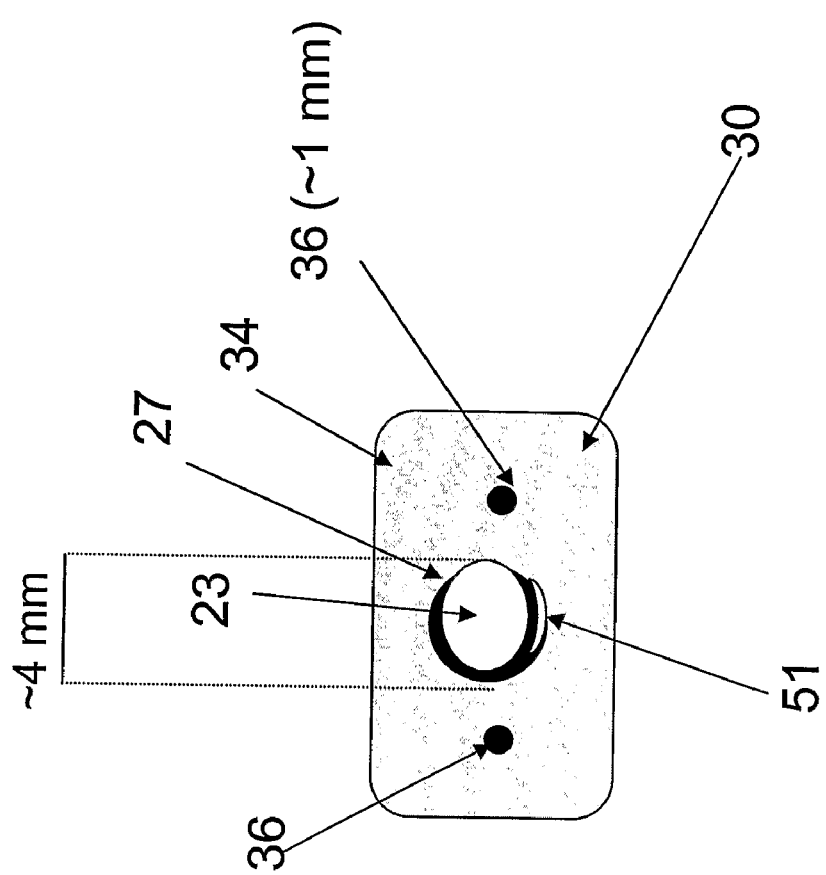
FIG. 6 is a plan bottom view of the distal end of the cardioplegia catheter of FIG. 1.
Figure 7:
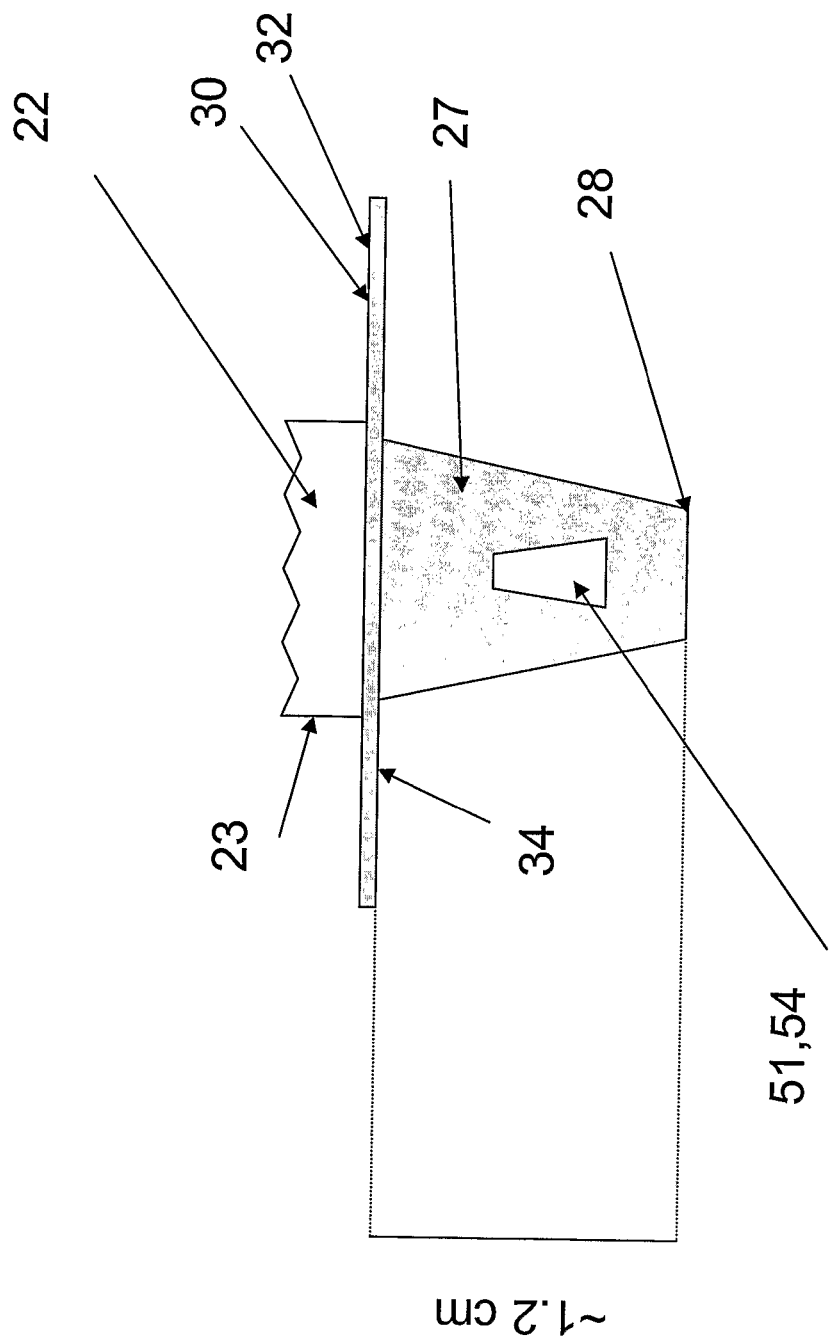
FIG. 7 is partial plan view of the distal end of the cardioplegia catheter of FIG. 1.

The present invention is more particularly described in the following exemplary embodiments that are intended as illustrative only since numerous modifications and variations therein will be apparent to those skilled in the art. As used herein, "a," "an," or "the" can mean one or more, depending upon the context in which it is used. The preferred embodiments are now described with reference to the figures, in which like reference characters indicate like parts throughout the several views.

Referring now to the figures, a first embodiment of a cardioplegia catheter system is illustrated. In one aspect, the cardioplegia catheter system 10 comprises a cardioplegia catheter 20, at least one stay suture 60, and at least one suture capture stylet 70. The catheter system can also comprise an insert needle 80. In an exemplary embodiment, the cardioplegia catheter 20 has an elongate tubular catheter body 22 that defines a continuous central lumen 24 therein. The central lumen extends from a proximal end 26 to a spaced distal end 28 of the catheter body. In one aspect, at least a portion of the catheter body is formed from a translucent material, such as, for example, a translucent polymer. In one aspect, a portion of the exterior surface of the catheter body tapers toward an opening defined by the central lumen at the distal end of the catheter body.

The central lumen 24 is constructed and arranged to allow for a fluid flow therethrough, such as, for example and not meant to be limiting, a cardioplegia solution, crystalloid solution, blood, or a combination thereof. A conventional luer-type of connector 21 is provided at the proximal end 26 of the catheter body, which is adapted for receiving in sealed fluid-tight communication the supply line(s) for the fluid(s) to be passed through the central lumen 24.

A flange 30 is connected to and extends therefrom the exterior surface 23 of the catheter body intermediate the tapered portion 27 of the exterior surface of the catheter body and the proximal end of the catheter body. Preferably, the flange 30 is connected to the exterior surface of the catheter body adjacent the tapered portion 27 of the distal end of the catheter body. In one aspect, the flange extends outwardly from the exterior surface of the catheter body and, in a further aspect, extends outwardly substantially perpendicular to the exterior surface. The flange has a top surface 32 and an opposed bottom surface 34. In one aspect, the flange may be substantially planar in shape. In an alternative aspect, at least a portion of the bottom surface 34 of the flange has a complementary shape to form a complementary fit against a portion of the exterior surface of the arterial vessel. The flange defines a plurality of suture openings 36 that extend therethrough the flange from the top surface to the bottom surface thereof. In one aspect, each suture opening 36 of the plurality of suture openings is spaced from the exterior surface 23 of the catheter body 22.

The catheter 20 further includes a plurality of longitudinally extending suture lumens (suture guides or rails) 40 that are connected to and spaced about the exterior surface of the catheter body. In one example, two suture lumens are provided and are spaced about 180 degrees apart so that they oppose each other on opposite sides of the exterior surface of the body. In other aspects, the suture lumens can be positioned substantially adjacent to each other or may be spaced up to the 180 degrees of separation. Each suture lumen 40 has a first end 42 and an opposed second end 44 and is formed as an elongate tube. In one aspect, the first end of each suture lumen is connected to the top surface 32 of the flange in overlying registration with one suture opening 36 of the plurality of suture openings in the flange. In another aspect, the second end 44 of the suture lumen can extend to the proximal end of the catheter body or can extend to a position intermediate the top surface of the flange and the proximal end of the catheter body. In one example, the interior diameter of the suture lumen 40 is greater than the diameter of the suture opening 36 in the flange.

In one embodiment, the catheter 20 also comprises a pressure lumen 50 that extends longitudinally at least partially between the proximal and distal ends of the catheter body 22. In one aspect, a portion of the exterior surface of the tapered portion 27 of the catheter body proximate the distal end defines a port 51 therein. The port is defined by an open bottom end 54 of the pressure lumen. In one aspect, a top end 52 of the pressure lumen can extend to the proximal end of the catheter body or can extend to a position intermediate the flange and the proximal end of the catheter body.

The pressure lumen 50 is in fluid communication with an elongated pressure line 55. One end of the pressure line is connected to the top end 52 of the pressure lumen. The opposite end of the pressure line is provided with a conventional luer-type of connector 53 that is adapted for receiving, in sealed fluid-tight communication, the fluid to be passed through the pressure lumen and the pressure line. As one will appreciate, the pressure lumen and the pressure line can be integrally formed.

In another embodiment, a pressure sensing device 120, such as a solid state pressure sensor, is positioned proximate the distal end of the catheter body. In this aspect, the electrical leads 122 from the sensing device can be adjacent to or incorporated into the wall of the catheter or sutures guides. The electronic leads can then be connected in known fashion to a suitable device for conversion of the electronic signal to a corresponding pressure value.

In use, the pressure line 55 may be operatively attached to a conventional pressure monitor, such as, for example and not meant to be limiting, a fluid-filled pressure transducer, for measurement of the cardioplegia delivery pressure. In an alternative example, the pressure line 55 may be operatively attached to a conventional cardioplegia delivery device, such as, for example, the Myocardial Protection System (MPS) by Quest Medical, Inc., so that the infusion rate of the cardioplegia solution via the central lumen of the catheter body maybe servo-controlled based on the pressure feedback information provided by the pressure line. The pressure line can also be connected to a standard pressure monitoring device in the operating room for visual and recordable appreciation of the pressure. In yet other example, the port 51 of the pressure lumen 50 can be used to vent the aorta of cardioplegia solution delivered retrograde or air before cross-clamp removal.

The at least one stay suture 60 of the cardioplegia catheter system 10 is a conventional medical biocompatible suture. In use, the number of stay sutures 60 required can depend upon the number of suture openings 36 in the flange of the catheter. Thus, in the illustrated example, in which there are two suture openings, one or two stay sutures can be provided. In another example, in which there are four suture opening, one, two, three or four stay sutures can be provided. In use, the stay sutures 60 are tacked to predetermined sites on the aortic root about and proximal to the selected aortic puncture site using a convention tacking methodology such as, for example, a purse-string suture technique. In one example, the stay sutures are positioned on the aortic root in the same relative spacing and orientation as the suture openings 36 in the flange 30 of the catheter.

In one aspect, the catheter 20 also comprises a means for releasably securing and fixing a portion of a stay suture 60 relative to the catheter. In one embodiment, the securing means comprises a plurality of cap members 100. In this aspect, each cap member is constructed and arranged for a friction fit with the second end of one suture lumen 40. Each cap member can have an elongated band 102 that is connected to a portion of the second end of its respective suture lumen such that, in operative use, the cap member can not be separated from the catheter (it can not be "dropped" into the operative field). In use, a portion of the stay suture 60 is manipulated and extended out of the second end 44 of the suture lumen 40 under tension. Subsequently, the cap member 100 is positioned into the second end in a friction fit, which results in a portion of the stay suture being captured and fixed between a portion of the second end and the cap member.

In an alternative embodiment, the securing means includes a clip 104 connected to a portion of the exterior surface of the second end of each respective suture lumen. The clip 104 is adapted to releasable grasp a portion of the stay suture. In another embodiment, the securing means comprises a bar member 106 connected to a portion of the exterior surface of the second end of each respective suture lumen. In this embodiment, a portion of the stay suture 60 is wrapped about the bar member to releasably fix the stay suture to the suture lumen 40. It is contemplated that one or more bar members can be provided for the user to wrap the corresponding sutures, or a combination of both the bar member and clip can be provided to wrap and snug the suture.

Each suture capture stylet 70 for use in the cardioplegia catheter system 10 comprises a handle 72 and a rod 74 extending from the handle that is adapted to fit within one of the suture lumens 40 of the catheter 20. The handle of the stylet may have a finger grip. In another aspect, at least a portion of the finger grip can be textured with a slip-free surface to prevent slippage with gloved hands. As noted above, the rod 74 of the capture stylet is sized to fit within the suture lumen of the catheter and is sufficiently long that a distal portion 76 of the rod can extend through the suture opening 36 in the flange and beyond the bottom surface of the flange while the handle of the extends beyond the second end 44 of the suture lumen. The distal portion 76 of the rod can, for example, have a hook shape or a spiral shape constructed and arranged for slideably grasping a portion of a stay suture. Other shapes for the distal portion 76 of the rod are contemplated. The shaped portion of the distal portion of the rod 74 is sized so that it can be drawn through the suture opening 36 in the flange and through the interior of the suture lumen 40. The rod of the stylet preferable is stiff but flexible. The rod 74 is sufficiently stiff to allow the distal portion 76 of the shaft to be steered by manipulating the handle. The rod is preferably made from a medical grade metal, such as, for example, a stainless steel (for example, SS 303 and SS304 stainless steel), or other suitable material, such as, for example, a polymer.

The catheter system 10 of the present invention can also comprise an insert needle 80. In one aspect, the insert needle comprises a lock end 82, an opposed puncture end 84, and a shaft 86 extending therebetween that is adapted to fit inside of the central lumen of the catheter body. In practice, the insert needle 80 can be provided premounted to the catheter body 22 to facilitate the proper installation of the catheter 20 onto the aortic arch. Alternatively, the insert needle 80 and the catheter 20 may be provided separately.

Figure 8:
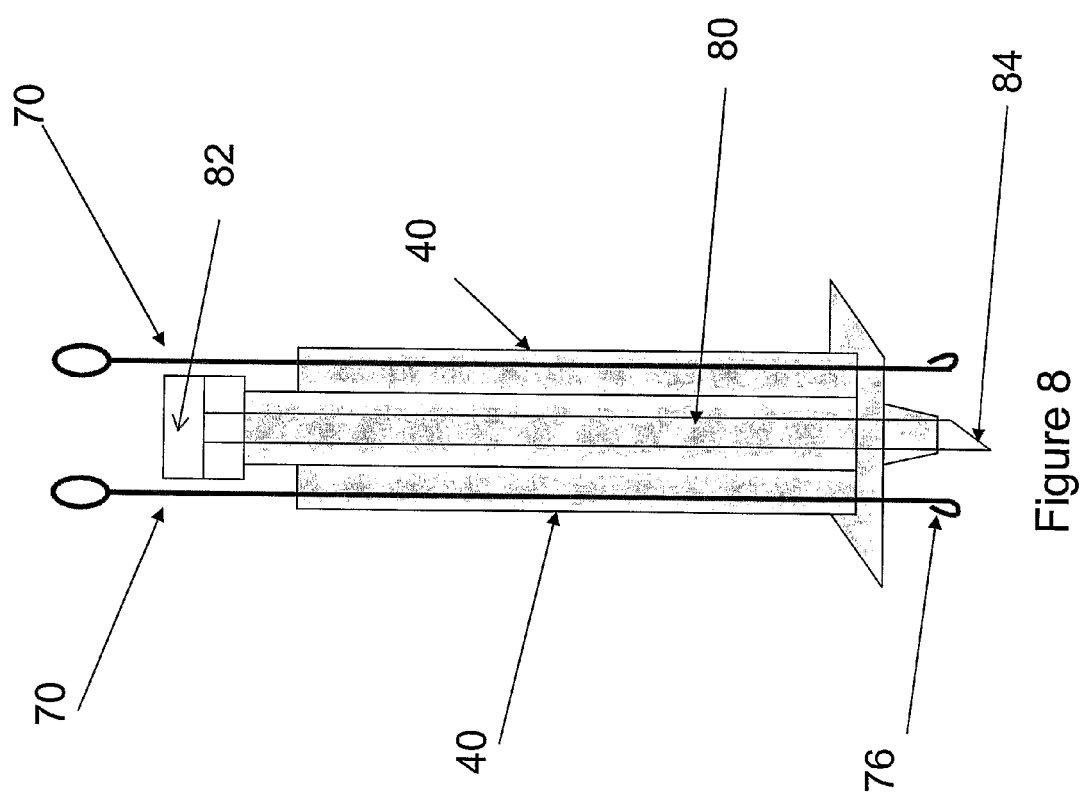
FIG. 8 is a partial cutaway view of the cardioplegia catheter system of FIG. 3, showing an insert needle disposed therein a central lumen of the cardioplegia catheter.

In one aspect, a connection device 88 is provided on the lock end 82 of the insert needle that is adapted for releasable connection to the proximal end 26 of the catheter body 22. For example, the connection device 88 may comprise a locking male luer fitting that may be releasably connected to a complementarily shaped female luer fitting on the proximal end of the catheter body. In one aspect, the shaft 86 of the insert needle is sized to fit in the central lumen 24 of the catheter body and is sufficiently long that the puncture end 84 of the insert needle is adjacent to, but extends therefrom, the opening defined by the central lumen in the distal end 28 of the catheter body 22 when the connection device is operatively engaged to the proximal end 26 of the catheter body. In a further aspect, the puncture end 84 has a tapered shape suitable for puncturing the wall of the aortic vessel. Exemplarily, the puncture end of the needle may be beveled, as shown in FIGS. 8 and 9, or conical with the point at the center of the puncture end.

The insert needle 80 also comprises a duct 90 that is in communication with a flash port 92 defined in the exterior surface of the insert needle and an orifice 94 defined in a portion of the puncture end. In one example, the flash port 92 is positioned intermediate the puncture end 84 and the lock end 82 of the insert needle. The shaft 86 of the insert needle is preferably made from a medical grade stainless steel, such as an SS 303 or SS 304 stainless steel, or other suitable material.

In another aspect, the insert needle also comprises an upper blood plug 96 and a lower blood plug 98. The lower blood plug 98 is positioned circumferentially about the exterior surface of the shaft of the insert needle below the flash port 92 and above the puncture end 94 of the insert needle. The lower blood plug is constructed and arranged so that portions of the peripheral edge of the lower blood plug sealingly engage portions of the interior surface of the central lumen such that blood that enters the central lumen between the opening in the distal end and the exterior surface of the insert needle remains trapped below the lower blood plug. The upper blood plug 98 is positioned circumferentially about the exterior surface of the shaft 86 of the insert needle above the flash port 92 and below the lock end 82 of the insert needle. Thus, the flash port is positioned between the upper and lower blood plugs. Similar to the lower blood plug, the upper blood plug is constructed and arranged so that portions of the peripheral edge of the upper blood plug sealingly engage portions of the interior surface of the central lumen so that blood that enters the central lumen through the flash port remains trapped between the upper and lower blood plugs. In use, the filing of the area between the upper and lower blood plugs is indicative of the needle penetrating the aorta, thereby signifying to the user that cardioplegia catheter can be advanced and secured in place by the stay sutures.

Operation

Using the illustrated example, a catheter 20, with the insert needle 80 already mounted thereto, and a pair of suture capture stylets 70 is preferably provided in a sterile package. As one will appreciate, single or double stay sutures can be accommodated, depending upon the surgeon's preference. In one example, the surgeon tacks a pair of purse string stay sutures 60 to the aortic root about to the determined aortic puncture site. Each suture capture stylet 70 is mounted within a respective suture lumen 40 with the distal portion 76 of the rod 74 extending beyond the bottom surface 36 of the flange of the catheter 20. As one will appreciate, the suture capture stylets 70 may be premounted in the suture lumens 40 in the delivered sterile package.

A portion of the distal portion 76 of each suture capture stylet 70 is positioned to snare a portion of a respective stay suture 60 and the capture stylets are drawn up through the suture lumens 40 such that the stay sutures are drawn up, through and out of the second end 44 of the respective suture lumens. The catheter 20 is then pushed down so that the puncture end 84 of the insert needle is brought into contact with the aortic puncture site. As noted above, filing of the space between the respective upper and lower blood plugs defines penetration of the aorta. Preferably, the catheter is guided to the aortic puncture site by pushing the catheter 20 along the extended and tensioned stay sutures 60 until the bottom surface 34 of the flange is seated on the exterior surface of the arterial vessel. Blood will pass through the duct 90 of the insert needle and will exit out of the flash port 92 when the puncture end 84 of the insert needle is positioned within the aortic vessel and in fluid communication with blood therein. Because at least a portion of the catheter body proximate the position of the flash port of the insert needle is formed of a translucent material, the surgeon will observe the blood exiting the flash port 92 and be assured that puncture end 94 of the insert needle and at least a portion of the tapered portion of the distal end of the catheter body is positioned within the interior of the vessel.

After the catheter 20 has been properly positioned, the stay sutures 60 are locked in place relative to the second end of the suture lumen by the securing means. The stay sutures 60 are under tension so that at least a portion of the tapered portion of the distal end 28 of the catheter body 22 is forced within the puncture wound formed by the puncture end of the insert needle and the bottom surface 34 of the flange is forced against the exterior surface of the arterial vessel. Placing the purse string stay sutures under tension acts to tighten the purse string sutures about and around the tapered portion of the distal end of the catheter body. In this fashion, hemostasis is maintained. The insert needle 80 can then be removed from the central lumen 24 of the catheter body and a conventional cardioplegia supply line is connected to the luer lock 21 at the proximal end 26 of the catheter body.

When the catheter 20 is to be removed, the stay sutures 60 are unlocked from the catheter. Upward tension is applied to the purse string stay sutures so that the edges of the puncture wound are substantially sealed about portions of the tapered portion of the distal end of the catheter body, which aids in maintaining hemostasis during the withdrawal of the catheter. The catheter is withdrawn upwards, preferably traveling along the tensioned stay sutures. As the tapered portion of the distal end of the catheter body is removed from the penetration site, the tension on the purse string stay sutures substantially simultaneously seals the penetration site to minimize loss of hemostasis. The catheter 20 is completely withdrawn from the stay sutures 60 and the stay sutures are conventional tied to close the puncture wound. Alternatively, the stay sutures can be inserted through asummel and be secured into position. Thus, the catheter 20 is readily removable while the stay sutures can remain intact for potential use of convention devices, for example, a basket, to capture atheromatous debris before the removal of the cross clamp.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure as defined by the appended claims.

What is claimed is:

1. A cardioplegia catheter system for delivery of a cardioplegia solution, comprising:
   a cardioplegia catheter comprising:
      an elongate tubular catheter body that defines a continuous central lumen, the central lumen extending from a proximal end to a spaced distal end;
      a flange that is connected to and extends therefrom an exterior surface of the catheter body intermediate the proximal and distal ends of the catheter body, the flange having a top surface and an opposed bottom surface, the top surface being closer than the bottom surface to the proximal end, wherein the flange defines at least one suture opening that extends therethrough the flange from the top surface to the bottom surface thereof; and
      at least one suture lumen being an elongate tube and extending from a first end proximate to the flange to a spaced second end, the at least one suture lumen extending parallel to the catheter body, the at least one suture lumen being disposed above the top surface of the flange, the first end of the at least one suture lumen being in an overlying registration with the at least one suture opening; and at least one suture capture stylet comprising a rod having a distal portion that is constructed and arranged to extend through the at least one suture opening in the flange of the catheter body and the at least one suture lumen, wherein the distal portion of the rod has a shape that is constructed and arranged for slideably grasping a portion of at least one stay suture.

2. The catheter system of claim 1, wherein at least a portion of the catheter body is formed from a translucent material.

3. The catheter system of claim 1, wherein the central lumen defines an opening at the distal end of the catheter body, and wherein at least a portion of the exterior surface of the catheter body is a tapered portion that tapers toward the opening defined by the central lumen at the distal end of the catheter body.

4. The catheter system of claim 3, wherein the flange is positioned adjacent to the tapered portion of the exterior surface and the distal end of the catheter body.

5. The catheter system of claim 1, wherein the flange extends outwardly substantially perpendicular from the exterior surface of the catheter body.

6. The catheter system of claim 1, wherein the flange is substantially planar.

7. The catheter system of claim 1, wherein at least one suture opening is spaced from the exterior surface of the catheter body.

8. The catheter system of claim 1, further comprising a connector that is adapted to receive a supply line for the cardioplegia solution and that is positioned at the proximal end of the catheter body.

9. The catheter system of claim 1, wherein:
the catheter further comprises a plurality of suture openings that extend through the flange from the top surface to the bottom surface thereof, and a plurality of extending suture lumens, each suture lumen is connected to, extends parallel to, and is positioned about the exterior surface of the catheter body, each suture lumen has a first end, an opposed second end and is an elongate tube, and
the first end of each suture lumen is connected to the top surface of the flange in an overlying registration with one suture opening of the plurality of suture openings in the flange of the catheter body.

10. The catheter system of claim 1, wherein the at least one suture lumen is positioned about the exterior surface of the catheter body, and the first end of the at least one suture lumen is connected to the top surface of the flange in the overlying registration with the at least one suture opening of.

11. The catheter system of claim 1, wherein the second end of the at least one suture lumen extends to the proximal end of the catheter body.

12. The catheter system of claim 1, wherein the second end of the suture lumen extends intermediate the top surface of the flange and the distal end of the catheter body.

13. The catheter system of claim 1, wherein the catheter further comprises a pressure lumen that extends longitudinally at least partially between the proximal and distal ends of the catheter body.

14. The catheter system of claim 13, wherein:
the central lumen defines an opening at the distal end of the catheter body,
at least a portion of the exterior surface of the catheter body is a tapered portion that tapers toward the opening defined by the central lumen at the distal end of the catheter body,
a portion of the exterior surface of the tapered portion of the catheter body defines a port therein, and the port is further defined by an open bottom end of the pressure lumen.

15. The catheter system of claim 14, wherein the pressure lumen is in fluid communication with an elongated pressure line.

16. The catheter system of claim 15, wherein the pressure lumen and the pressure line are integrally formed.

17. The catheter system of claim 1, further comprising a pressure sensing device positioned proximate the distal end of the catheter body, the pressure sensing device adapted for sensing a pressure of fluid proximate the distal end of the catheter body.

18. The catheter system of claim 1, further comprising a means for releasably securing and fixing a portion of the stay suture relative to the catheter body.

19. The catheter system of claim 18, wherein the means for releasably securing and fixing a portion of the stay suture relative to the catheter body comprises at least one cap member, the at least one cap member being constructed and arranged for a friction fit with the second end of the at least one suture lumen.

20. The catheter system of claim 19, wherein the at least one cap member has a band connected to a portion of the second end of the at least one suture lumen.

21. The catheter system of claim 18, wherein the means for releasably securing and fixing a portion of the stay suture relative to the catheter body comprises a clip connected to a portion of the exterior surface of the second end of the at least one suture lumen.

22. The catheter system of claim 18, wherein the means for releasably securing and fixing a portion of the stay suture relative to the catheter body comprises at least one bar member connected to a portion of the exterior surface of the second end of the at least one respective suture lumen.

23. The catheter system of claim 1, wherein the at least one suture capture stylet further comprises a handle that is connected to the rod, and wherein the handle of the at least one suture capture stylet forms a finger grip.

24. The catheter system of claim 1, wherein the rod of the at least one suture capture stylet is adapted to fit within the at least one suture lumen.

25. The catheter system of claim 24, wherein the at least one suture lumen has a first length and the rod has a second length, and wherein the second length of the rod is at least as long as the first length of the suture lumen.

26. The catheter system of claim 1, wherein the shaped portion of the distal portion of the rod is sized and shaped so that it can be drawn through the suture opening in the flange and through an interior of the suture lumen.

27. The catheter system of claim 1, further comprising an insert needle having a lock end, an opposed puncture end, and a shaft extending therebetween the lock end and the puncture end.

28. The catheter system of claim 27, wherein the insert needle is constructed and arranged for insertion therein the central lumen of the catheter body.

29. The catheter system of claim 28, wherein a connection device is formed on the lock end of the insert needle for releasable connection to the proximal end of the catheter body.

30. The catheter system of claim 29, wherein the central lumen defines an opening at the distal end of the catheter body, and wherein the insert needle is sized such that the puncture end of the insert needle extends therefrom the opening defined by the central lumen in the distal end of the catheter body when the connection device is operatively engaged to the proximal end of the catheter body.

31. The catheter system of claim 27, wherein the puncture end has a tapered shaped.

32. The catheter system of claim 27, wherein the insert needle further comprises a duct that is in communication with a flash port defined in an exterior surface of the insert needle and an orifice defined in a portion of the puncture end of the insert needle.

33. The catheter system of claim 32, wherein the flash port is positioned intermediate the puncture end and the lock end of the insert needle.

34. The catheter system of claim 32, wherein the insert needle further comprises a lower blood plug positioned circumferentially about the exterior surface of the shaft of the insert needle below the flash port and above the puncture end of the insert needle.

35. The catheter system of claim 34, wherein the lower blood plug is constructed and arranged so that portions of a peripheral edge of the lower blood plug sealingly engage portion of an interior surface of the central lumen such that fluid that enters the central lumen between the opening in the distal end of the central lumen and the exterior surface of the insert needle remains trapped below the lower blood plug.

36. The catheter system of claim 34, wherein the insert needle further comprises an upper blood plug that is positioned circumferentially about the exterior surface of the shaft of the insert needle above the flash port and below the lock end of the insert needle.

37. The catheter system of claim 36, wherein the upper blood plug is constructed and arranged so that portions of a peripheral edge of the upper blood plug sealingly engage portion of an interior surface of the central lumen such that fluid that enters the central lumen through the flash port, positioned between the upper and lower blood plugs, remains trapped between the upper and lower blood plugs.

38. A cardioplegia catheter system for delivery of a cardioplegia solution, comprising:
  a cardioplegia catheter comprising:
    an elongate tubular catheter body that defines a continuous central lumen, the central lumen extending from a proximal end to a spaced distal end;
    a flange that is connected to and extends therefrom an exterior surface of the catheter body intermediate the proximal and distal ends of the catheter body, the flange having a top surface and an opposed bottom surface, the top surface being closer than the bottom surface to the proximal end, wherein the flange defines at least one suture opening that extends therethrough the flange from the top surface to the bottom surface thereof; and
    at least one suture lumen extending from a first end proximate to the distal end to a spaced second end, the at least one suture lumen extending parallel to the catheter body and being an elongate tube,
    wherein the at least one suture lumen extends to the top surface of the flange, and the first end of the at least one suture lumen is disposed above the top surface of the flange in an overlying registration with the at least one suture opening in the flange of the catheter body.

39. The catheter system of claim 38, further comprising:
  at least one suture capture stylet comprising a rod having a distal portion that is constructed and arranged to extend through the at least one suture lumen and the at least one suture opening in the flange of the catheter body, wherein the distal portion of the rod has a shape that is constructed and arranged for slideably grasping a portion of at least one stay suture,
  wherein the at least one suture lumen is positioned about the exterior surface of the catheter body.

* * * * *